United States Patent
Holm et al.

(10) Patent No.: US 10,077,222 B2
(45) Date of Patent: Sep. 18, 2018

(54) PROCESS FOR THE PREPARATION OF ETHYLENE GLYCOL FROM SUGARS

(71) Applicant: Haldor Topsøe A/S, Kgs. Lyngby (DK)

(72) Inventors: Martin Spangsberg Holm, Oxford (GB); Esben Taarning, Frederiksberg (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/322,680

(22) PCT Filed: Jun. 29, 2015

(86) PCT No.: PCT/EP2015/064741
§ 371 (c)(1),
(2) Date: Dec. 28, 2016

(87) PCT Pub. No.: WO2016/001169
PCT Pub. Date: Jan. 7, 2016

(65) Prior Publication Data
US 2017/0137354 A1    May 18, 2017

(30) Foreign Application Priority Data

Jun. 30, 2014 (EP) .................................... 14174972
Jun. 30, 2014 (EP) .................................... 14174976

(51) Int. Cl.
| | | |
|---|---|---|
| C08G 63/02 | (2006.01) |
| C07C 29/145 | (2006.01) |
| C07C 45/52 | (2006.01) |
| C07C 29/76 | (2006.01) |
| B01J 6/00 | (2006.01) |

(52) U.S. Cl.
CPC ............. C07C 29/145 (2013.01); B01J 6/008 (2013.01); C07C 29/76 (2013.01); C07C 45/52 (2013.01)

(58) Field of Classification Search
USPC .......................... 525/165; 528/308.3, 308.8
See application file for complete search history.

(56) References Cited

U.S. PATENT DOCUMENTS

| | | |
|---|---|---|
| 4,321,414 A | 3/1982 | Costa |
| 5,252,188 A | 10/1993 | Stradal et al. |
| 2011/0046419 A1 | 2/2011 | Zhang et al. |
| 2011/0312051 A1 | 12/2011 | Kalnes et al. |
| 2012/0172633 A1 | 7/2012 | Zhang et al. |
| 2015/0329449 A1 | 11/2015 | Schreck et al. |

FOREIGN PATENT DOCUMENTS

| | | |
|---|---|---|
| WO | WO 02/40436 A1 | 5/2002 |
| WO | WO 2013/015996 A2 | 1/2013 |
| WO | WO 2014/131743 A1 | 9/2014 |

OTHER PUBLICATIONS

R. Ooms et al., "Conversion of Sugars to Ethylene Glycol with Nickel tungsten Carbide in a Fed-Batch Reactor: High Productivity and Reaction Network Elucidation." Green Chemistry, vol. 16, pp. 695-707, 2014.
Database WPI Week 201062, Thomson Scientific, London, GB; AN 2010-K68308, XP002729927, & CN 101 781 168 A (N. Xian) Xi 'an Modern Chem. Res. Inst., Jul. 21, 2010. Abstract.
Database WPI, Week 200682, Thomson Scientific, London, GB; AN 2006-798778, XP002729928, & CN 1 762 938 A (C. Xu), Apr. 26, 2006. Abstract.

*Primary Examiner* — Terressa Boykin
(74) *Attorney, Agent, or Firm* — Blank Rome LLP

(57) ABSTRACT

A process for the preparation of ethylene glycol comprising the steps of pyrolyzing a monosaccharide and hydrogenating the product composition in the presence of a catalyst and a solvent, wherein the pressure of the hydrogenation reaction is 40 bar or greater.

17 Claims, No Drawings

PROCESS FOR THE PREPARATION OF ETHYLENE GLYCOL FROM SUGARS

BACKGROUND

Ethylene glycol can be prepared by a variety of routes including from monosaccharides, e.g. sugars, via fermentation and hydrogenolysis processes, or by hydroformylation.

The fermentation route is a five-step process wherein glucose is fermented to ethanol and carbon dioxide, followed by conversion of ethanol to ethylene, ethylene to ethylene oxide and ethylene oxide to ethylene glycol. One disadvantage of this method is that per mole of glucose fermented, two moles of carbon dioxide are produced together with two moles of ethanol; this has the effect that a theoretical maximum of 67% of the carbon present in the glucose can be transformed to ethanol.

The hydrogenolysis route is a two-step process wherein glucose is reduced to sorbitol followed by hydrogenolysis of sorbitol to ethylene glycol, as illustrated by U.S. Pat. No. 6,297,409B1 and US 2008/0228014 A1. Significant quantities of propylene glycol, compared to ethylene glycol, are formed via the hydrogenolysis process. Additionally, the amount of catalyst used is significant and appears difficult to reactivate once spent. Furthermore, the byproducts formed, in particular butanediols, are difficult to separate from the desired product. In particular, the industrially favorable method of distillation for separation (purification) purposes is extremely difficult to apply as the byproducts have very similar boiling points to the final product, and the desired product may react further, as illustrated in US2014/0039224 A1 and U.S. Pat. No. 5,393,542 B1.

The hydroformylation route is a two-step route wherein glycolaldehyde is prepared from formaldehyde, carbon monoxide and hydrogen, followed by hydrogenation of the glycolaldehyde to ethylene glycol, as illustrated in U.S. Pat. No. 4,496,781 B1. There appears to be several extraction steps present in order to separate formaldehyde from glycolaldehyde and proceed with the hydrogenation reaction.

Therefore it is desirable to provide an alternative, improved, high yielding and industrially feasible process for the preparation of ethylene glycol from sugars. An additional advantage would be the use of greater than 67% of the sugar carbon atoms present in the final product or a commercially valuable byproduct.

It could be conceived that ethylene glycol may be prepared via a process comprising two steps; such as the preparation of glycolaldehyde from sugars and its subsequent hydrogenation to glycols. The two steps of the proposed processes appear to be independently successful as illustrated in the following paragraphs.

It is known that sugars may be pyrolysed to obtain a pyrolysis product composition comprising oxygenate compounds such as glycolaldehyde U.S. Pat. No. 7,094,932 B2; the pyrolysis product composition typically comprises $C_1$-$C_3$ oxygenate compounds, including formaldehyde, glycolaldehyde, glyoxal, pyruvaldehyde and acetol. The main product of this reaction is glycolaldehyde (U.S. Pat. No. 7,094,932 B2). Water is the solvent of the reaction.

It is also known that pure glycolaldehyde may be hydrogenated to ethylene glycol. U.S. Pat. No. 4,200,765 B1 discloses hydrogenation of glycolaldehyde under severe conditions: at high pressure [3000 psi (ca. 345 bar)], high temperature [150° C.], with an organic solvent [N-methyl pyrrolidine] and a palladium on carbon [Pd/C] catalyst for a prolonged period [5 h]. U.S. Pat. No. 4,321,414 B1 and U.S. Pat. No. 4,317,946 B1 disclose the hydrogenation of glycolaldehyde with a homogenous ruthenium catalyst and U.S. Pat. No. 4,496,781 B1 discloses a continuous flow hydrogenation at low pressure [500 psi (ca. 35 bar)], at high temperature [160° C.] with a ruthenium on carbon catalyst [Ru/C] in ethylene glycol and trace acetonitrile as solvent.

As illustrated, the two steps, pyrolysis of glucose to obtain, inter alia glycolaldehyde, and hydrogenation of pure glycolaldehyde, appear to be independently possible. However, in order for the pyrolysis product composition to be hydrogenated, laborious separation processes must be employed to remove formaldehyde from the pyrolysis product composition as formaldehyde is a known poison of hydrogenation catalysts U.S. Pat. No. 5,210,337 B1. U.S. Pat. No. 5,393,542 B1 discloses an exemplary purification process comprising multiple distillation steps followed by a solvent-induced precipitation to obtain glycolaldehyde. Therefore, it is not possible to hydrogenate the product of the pyrolysis step (the pyrolysis product composition) directly, as formaldehyde is present in the composition in a significant amount.

In addition to the requirement of removing formaldehyde, which would increase the number of process steps required, it would also be a great advantage industrially to use a solvent that is non-toxic, for example water. Therefore it would be a significant advantage to be able to carry out the hydrogenation step in the presence of formaldehyde, using a non-toxic solvent and in the solvent of the previous (pyrolysis) reaction.

With regard to hydrogenation of glycolaldehyde, although there is the provision of suitable reaction conditions to obtain a high yield in organic solvents, the reaction with water as a solvent appears to be less successful. U.S. Pat. No. 5,393,542 B1 discloses thermal degradation of glycolaldehyde (2-hydroxyacetaldehyde) when subjected to temperatures of 90° C. or higher and where water is the solvent.

EP 0 002 908 B1 discloses the variation in yield (conversion and selectivity) of the hydrogenation of glycolaldehyde reaction with the use of various catalysts in an aqueous solution at 110° C.: Raney Nickel [100% conversion 49.4% selectivity], 10% Pd/C [62% conversion, 61% selectivity] and 10% Pt/C [100% conversion, 73% selectivity]. An additional disadvantage of catalysts used in liquid water is the strain on the catalyst. In particular, at high temperatures (>160° C.) many supports are not stable and will dissolve, degrade or the surface area is reduced; Energy & Fuels 2006, 20, 2337-2343. Hence, special catalysts are needed and the long-term catalyst performance is often problematic, consequently, the catalyst must be replaced frequently (ca. 3-6 months). Consequently, mild reaction conditions are favorable in order to ensure longevity of the catalyst, in particular on an industrial scale and in industrial conditions.

In addition, the choice of catalyst may affect the decomposition of glycolaldehyde when in the presence of the catalyst; U.S. Pat. No. 5,210,337 B1 discloses the problem of glycolaldehyde 'unzipping' to form formaldehyde and consequently poisoning the hydrogenation catalyst. It is also possible that glycolaldehyde may self-condense or condense with another $C_1$-$C_3$ oxygenate compound, also illustrated in U.S. Pat. No. 5,210,337 B1. Additionally, the choice of catalyst and stability of the glycol product may affect the degree of reduction of the glycolaldehyde. It is possible that a catalyst may reduce the glycolaldehyde to ethanol or ethane, i.e. over reduce the glycolaldehyde.

Additionally, it is known that an increase in temperature, concentration of the substrate and amount and identity of catalyst present affects the yield (conversion and selectivity) of hydrogenation reactions of glycolaldehyde. Handbook of Heterogeneous Catalytic Hydrogenation for Organic Synthesis, Shigeo Nishimura, ISBN: 978-0-471-39698-7, April 2001.

As demonstrated, an industrial scale process for preparing ethylene glycol from sugars via pyrolysis of sugars and subsequent hydrogenation is hindered from two perspectives. The first is the requirement to remove formaldehyde from the pyrolysis product composition in order to enable successful hydrogenation. The second is the provision of mild reaction conditions that are high yielding. Furthermore, in order to provide a process that is industrially and commercially feasible, it is desirable to provide a high yielding two-step process that utilizes non-toxic solvents and produces a minimal amount of byproducts that are separable from the ethylene glycol product using industrially feasible techniques. The ability to separate byproducts from the ethylene glycol product enables the ethylene glycol to be used in processes such as polymer production. Polymer production requires substrates to be in a highly pure form.

It has now been discovered that the pyrolysis product composition obtainable from the pyrolysis of sugars may be hydrogenated in a high yield, in mild conditions, with minimal byproducts and directly from a pyrolysis product composition comprising formaldehyde.

DISCLOSURE OF THE INVENTION

It has been discovered that it is possible to subject the pyrolysis product composition obtainable from the pyrolysis of sugars to hydrogenation conditions and to obtain a high yield (high conversion and high selectivity) in mild reaction conditions and with minimal byproducts and without removing formaldehyde (i.e. $C_1$-oxygenate compounds) prior to the hydrogenation reaction. Furthermore, it has been discovered that ethylene glycol is more stable at higher pressures and temperatures and a smaller amount of the byproduct 1,2-butanediol is produced.

The present invention provides a process for the preparation of a composition comprising ethylene glycol comprising the steps of:
 a. Pyrolysing a sugar to obtain a pyrolysis product composition; and
 b. Hydrogenating the pyrolysis product composition of step a. in the presence of a catalyst, hydrogen and a solvent to obtain a (hydrogenated) product composition.
 c. Optionally separating (purifying) ethylene glycol from the (hydrogenated) product composition obtained in step b.

An aspect of the present invention is the presence of $C_1$-oxygenates present in Step a. Step a. may read: Pyrolysing a sugar to obtain a pyrolysis product composition comprising $C_1$-oxygenates. Alternatively, step a. may read: Pyrolysing a sugar to obtain a pyrolysis product composition comprising formaldehyde.

The product of the present invention may be the (hydrogenated) product composition of step b. comprising ethylene glycol. (Hydrogenated) product composition means the product of step b. comprising ethylene glycol. The (hydrogenated) product composition of step b. may further comprise unreacted substrate. Alternatively, the product of the present invention may be the product of step b. that has been purified, i.e. the product of step c.

Sugar means one or more sugars selected from the group consisting of monosaccharides and disaccharides; preferably, sugar means one or more sugars selected from the group consisting of glucose, sucrose, fructose, xylose, mannose, arabinose and galactose. Preferably the sugar is a monosaccharide and is glucose. The sugar may be in the form of a solution, wherein the sugar solution comprises a sugar and a solvent.

The solvent of the sugar solution is a solvent selected from the group consisting of: water or water and alcohol. Alcohol means one or more alcohol selected from the group consisting of methanol and ethanol. For example, the sugar solution may be present as an aqueous sugar solution, preferably an aqueous glucose solution.

The solvent of step b. is a solvent selected from the group consisting of: water; alcohol or water and alcohol. Alcohol means one or more alcohol selected from the group consisting of methanol, ethanol, ethylene glycol and propylene glycol.

The solvent of step b. may be a mixture of water and alcohol. Where the solvent is water and alcohol, the water and alcohol are in a ratio of equal to or greater than 95:5, 90:10, 80:20, 70:30, 60:40, 50:50, 40:60 and 30:70.

The pyrolysis product composition of step a. may also be known as a crude pyrolysis product composition. The pyrolysis product composition comprises oxygenate compounds such as glycolaldehyde and may be prepared according to U.S. Pat. No. 7,094,932 B2. The pyrolysis product composition comprises $C_1$-$C_3$ oxygenate compounds. $C_1$-$C_3$ oxygenate compounds means oxygenated compounds comprising a carbon chain length of one, two or three carbon atoms. For example, $C_1$ oxygenate compounds comprise a carbon chain length of one carbon atom, such as formaldehyde and formic acid; $C_2$ oxygenate compounds comprise a carbon chain length of two carbon atoms, such as glycolaldehyde, glyoxal and acetic acid; $C_3$ oxygenate compounds comprise a carbon chain length of three carbon atom, such as pyruvaldehyde and acetol. $C_1$-$C_2$ oxygenate compound composition means a composition comprising one or more compounds selected from the group consisting of formaldehyde, glycolaldehyde, glyoxal, pyruvaldehyde and acetol. Preferably the pyrolysis product composition comprises $C_2$ oxygenate compounds. Typically, the $C_2$-oxygenate compound component of the composition comprising $C_1$-$C_2$ oxygenate compounds is for example 10 wt % or greater, 30 wt % or greater. Where the pyrolysis product composition of step a. comprises formaldehyde and glycolaldehyde, the wt/wt ratio of the formaldehyde to glycolaldehyde present in the pyrolysis product composition of step a. may be from about 1:2 to about 1:20; from 1:2 to 1:20; from 1:7 to 1:14; from 1:8 to 1:12; from 1:9 to 1:10. The range from 1:2 to 1:20 may comprise the range from 1:2 to 1.69; from 1:2 to about 1:7; from 1:2 to 1:7. The range from 1:2 to 1:20 may comprise the range from 1:14 to 1:20; from about 1:14 to 1:20; from 1:14.1 to 1:20. The wt/wt ratio of the formaldehyde to glycolaldehyde present in the pyrolysis product composition of step a. may be from 1:2 to 1:20, for example for pyrolysis product compositions obtainable from xylose and fructose sugar substrates.

The hydrogenation of step b. is carried out in the presence of a catalyst comprising a catalyst metal component such as ruthenium, ruthenium alloy, palladium, platinum or nickel. The catalyst metal component is supported by a support such as carbon. Known catalysts include ruthenium on a carbon support. For example, the hydrogenation of step b. may be carried out in the presence of a catalyst such as ruthenium on a carbon support catalyst. For example, the hydrogenation of step b. may be carried out in the presence of catalyst such as a 5% or 10% ruthenium on a carbon support catalyst. Examples of ruthenium alloy catalysts comprising 0.5-2% ruthenium are disclosed in WO 2014/066052 A1.

The catalyst of step b. may be present in the reaction solution in a wt/wt ratio of formaldehyde:catalyst metal component of from 1:1 to 15:1, from 1:1 to 11:1; from 1:1 to 10:1; from 1:1 to 7:1; from 1:1 to 5:1; from 3.0:1 to 15:1; from 3.1:1 to 15:1; from 3.2:1 to 15:1.

The hydrogenation of step b. may be carried out at a pressure of from about 30 bar to 90 bar, from 30 bar to 120 bar, from 40 bar to 120 bar, from 40 bar to 140 bar, from about 90 bar to 150 bar, preferably from 50 bar to 150 bar. Pressure means hydrogen partial pressure.

The hydrogenation of step b. may be carried out at a temperature of from 40 to 160° C., from 50 to 140° C., from 60 to 130° C., preferably from 80 to 120° C.

The yield (conversion and selectivity) of ethylene glycol from $C_2$-oxygenate compounds of the pyrolysis product of step a. is greater than 40%, greater than 50%, greater than 70%.

The conversion of $C_2$-oxygenate compounds of the pyrolysis product composition of step a. to ethylene glycol (step b.) may be 70% or greater; 80% or greater.

Conversion means the transformation of $C_2$-oxygenate compounds of the pyrolysis product composition to another compound or compounds.

The selectivity of $C_2$-oxygenate of the pyrolysis product composition of step a. to ethylene glycol may be 75% or greater, 85% or greater, preferably 95% or greater.

Selectivity means the transformation of $C_2$-oxygenate compounds of the pyrolysis product composition to ethylene glycol rather than other compounds such as ethanol or ethane.

The product of step b. comprises a 1,2-butanediol (1,2-BDO):ethylene glycol wt/wt ratio may be equal to or less than 0.01:1, 0.005:1, 0.004:1, 0.003:1.

The process of the present invention is two steps. 'Two step' process means the conversion of sugars to ethylene glycol via two chemical transformations: the pyrolysis of sugars and the hydrogenation of glycolaldehyde obtainable from the pyrolysis of glucose. A further embodiment of the present invention is a two-step process wherein the pyrolysis product composition of step a. is directly hydrogenated in step b. For example the pyrolysis product composition of step a. comprising $C_1$-$C_3$ oxygenate compounds is used as the starting composition for the hydrogenation step (step b.). For example, the product of step a. is hydrogenated.

Purifying means separating the specific chemical products of the (hydrogenated) product composition of step b, e.g. separating ethylene glycol, propylene glycol and other components. Exemplary separation processes are disclosed in U.S. Pat. No. 8,177,980 B2 and US 2014/0039224 A1. Such separation (purification) processes may be chromatography and distillation.

Ethylene glycol prepared according to the present invention may be used as a chemical. For example, ethylene glycol may be used as a monomer in the preparation of polymers including polyethylene terephthalate (PET), polyester resins, fibers and films. Ethylene glycol may also be used as a deicing agent, coolant, in particular in refrigeration apparatus, antifreeze agent or solvent. As described on: http://www.dow.com/ethyleneglycol/prod/meg.htm

EXAMPLES

Example 1

A pyrolysis product composition comprising $C_1$-$C_3$ oxygenate compounds was obtained by pyrolysis of a 10 wt % aqueous glucose (D-glucose monohydrate; Sigma Aldrich) solution as described in U.S. Pat. No. 7,094,932 B2. The composition of the pyrolysis product composition is given in Table 1.

TABLE 1

Composition of the pyrolysis product composition of Example 1.

| Glycolaldehyde | Glyoxal | Pyruvaldehyde | Formaldehyde | Acetol |
|---|---|---|---|---|
| 63.4 g/l | 4.7 g/l | 8.6 g/l | 7.7 g/l | 2.3 g/l |

Examples 2-4

The pyrolysis product composition of Example 1 and described in Table 1 (15.5 g) was loaded into an autoclave along with 5% Ru on carbon catalyst (Sigma Aldrich, 0.20 g). The autoclave was purged 3 times with hydrogen and subsequently pressurized with hydrogen to the respective pressures given in Table 2. The mixture was heated to 80° C. from room temperature over the course of 15 min and stirred for 6 hours. The autoclave was then cooled to room temperature and the decrease in hydrogen pressure was noted.

The hydrogenated product mixture was isolated from the catalyst by filtration and analyzed by HPLC and GC.

The maximum theoretical yield of ethylene glycol was based on hydrogenation of both glyoxal and glycolaldehyde to ethylene glycol.

TABLE 2

| | $H_2$ pressure (bar) | Temperature (° C.) | Time (h) | Catalyst loading | Yield of ethylene glycol (%) | Formaldehyde/catalyst ratio (wt/wt) | 1,2-BDO/ethylene glycol |
|---|---|---|---|---|---|---|---|
| Ex 2 | 15 | 80 | 6 | 0.2 g | 12.3% | 0.6 | — |
| Ex 3 | 30 | 80 | 6 | 0.2 g | 18.9% | 0.6 | — |
| Ex 4 | 90 | 80 | 6 | 0.2 g | 88.8% | 0.6 | 0.0021 |

Examples 2-4 illustrate the significantly increased yield of ethylene glycol with an increase in reaction pressure. Additionally Example 4 demonstrates the low yield of 1,2-BDO produced by the process of the present invention in comparison to the preparation of ethylene glycol via the hydrogenolysis route as illustrated by US 20080228014 A1 [1,2-BDO:ethylene glycol ratio of 0.08].

Examples 5-8

The method as described in Examples 2-4 was repeated using either ethylene glycol or propylene glycol as the substrate [pyrolysis product composition of Example 1] with a pressure of either 30 or 90 bar, a temperature of either 120° C. or 140° C. and a reaction duration of 3 hours. Results are provided in Table 3.

TABLE 3

| | | $H_2$ pressure (bar) | Temperature ° C. | Time (h) | Recovery of glycol |
|---|---|---|---|---|---|
| Ex 5 | Ethylene glycol | 30 | 140 | 3 | 59.4% |
| Ex 6 | Ethylene glycol | 90 | 140 | 3 | 87.7% |

TABLE 3-continued

|  |  | H$_2$ pressure (bar) | Temperature ° C. | Time (h) | Recovery of glycol |
|---|---|---|---|---|---|
| Ex 7 | Propylene glycol | 30 | 120 | 3 | 87.8% |
| Ex 8 | Propylene glycol | 90 | 120 | 3 | 96.0% |

Table 3 shows an increased stability of ethylene glycol and propylene glycol with an increase in pressure under hydrogenation reaction conditions.

Example 9

Glycol aldehyde dimer (1.0 g) was dissolved in demineralized water (14.5 g). The solution was loaded into an autoclave along with 5% Ru on carbon catalyst (Sigma Aldrich, 0.20 g). The autoclave was purged 3 times with hydrogen and subsequently pressurized with hydrogen to the respective pressures given in Table 2. The mixture was heated to 80° C. from room temperature in the course of 15 min and stirred for 3 hours. The autoclave was then cooled to room temperature and the decrease in hydrogen pressure was noted.

The product mixture was isolated from the catalyst by filtration and analyzed by HPLC and GC.

Example 10

The method of Example 9 was repeated under a pressure of 90 bar.

Example 11

The method of Example 9 was repeated at a temperature of 100° C.

Results of Examples 9 to 11 are provided in Table 4. The amount of 1,2-butanediol (1,2-BDO) present in relation to ethylene glycol is provided. It can be seen that an increase in pressure of the reaction results in a reduction of 1,2-butanediol (1,2-BDO) formed, resulting in an increased purity of the ethylene glycol product in milder conditions.

TABLE 4

|  | H$_2$ pressure (bar) | Temp. (° C.) | Time (h) | Catalyst loading (g) | Yield of ethylene glycol (wt %) | 1,2-BDO/ ethylene glycol |
|---|---|---|---|---|---|---|
| Ex 9 | 90 | 80° C. | 3 | 0.2 g | >98% | 0.000045 |
| Ex 10 | 30 | 80° C. | 3 | 0.2 g | 95% | 0.00025 |
| Ex 11 | 30 | 100° C. | 3 | 0.2 g | 90% | 0.00098 |

The invention claimed is:

1. A process for the preparation of ethylene glycol comprising the steps of:
   a. pyrolysing a sugar to obtain a pyrolysis product composition comprising formaldehyde; and
   b. hydrogenating the pyrolysis product composition in the presence of a catalyst and a solvent,
   wherein hydrogenation pressure of the reaction of step b. is 40 bar or greater.

2. A process according to claim 1, wherein the product of hydrogenation reaction is purified.

3. A process according to claim 1, wherein the sugar comprises one or more sugars selected from the group consisting of glucose, sucrose, fructose, xylose, mannose, arabinose and galactose.

4. A process according to claim 1, wherein the solvent is selected from the group consisting of water, alcohol and water and alcohol.

5. A process according to claim 4, wherein the alcohol is selected from one or more of the group consisting of methanol, ethanol, ethylene glycol and propylene glycol.

6. A process according to claim 1, wherein the pyrolysis product composition comprises one or more C$_{2-3}$ oxygenate compounds selected from the group consisting of glycolaldehyde, glyoxal, pyruvaldehyde and acetol.

7. A process according to claim 1, wherein the catalyst comprises a metal component selected from the group consisting of ruthenium, ruthenium alloy, palladium, platinum and nickel.

8. A process according to claim 1, wherein the catalyst metal component is present in a ratio of formaldehyde:catalyst metal component of from 1:1 to 1:15.

9. A process according to claim 1, wherein the hydrogenation is carried out at a pressure of from 40 bar to 120 bar.

10. A process according to claim 1, wherein the hydrogenation is carried out at a temperature of from 40° C. to 160° C.

11. A process according to claim 1, wherein the conversion of C$_2$ oxygenate compounds to ethylene glycol of the hydrogenation is at least 70%.

12. A process according to claim 1, wherein the selectivity of C$_2$ oxygenate compounds to ethylene glycol of step b. is at least 75%.

13. A process according to claim 1, wherein the pyrolysis product composition of step a. comprises formaldehyde in a ratio of formaldehyde:glycolaldehyde of from 1:2 to 1:20.

14. A process according to claim 1, wherein the product of the hydrogenation comprises a 1,2-butanediol:ethylene glycol wt/wt ratio of equal to or less than 0.01:1.

15. A process according to claim 1, wherein the process is a two-step process and the pyrolysis product composition of step a. is directly hydrogenated in step b.

16. A process according to claim 1, wherein the pyrolysis product composition comprises one or more C$_2$ oxygenate compounds selected from the group consisting of glycolaldehyde, glyoxal and acetic acid.

17. A process according to claim 8, wherein the C$_2$-oxygenate compound of the composition comprising C$_1$-C$_3$ oxygenate compounds is 10 wt % or greater.

* * * * *